US012567020B1

(12) United States Patent
Alrabiaah et al.

(10) Patent No.: US 12,567,020 B1
(45) Date of Patent: Mar. 3, 2026

(54) SYSTEM AND METHOD FOR DELIVERING MEDICATION AND MEDICAL SUPPLIES TO PERSONS IN NEED THEREOF IN RESPONSE TO A LARGE SCALE EMERGENCY SCENARIO

(71) Applicant: KING SAUD UNIVERSITY, Riyadh (SA)

(72) Inventors: Sumayah Abdulaziz Alrabiaah, Riyadh (SA); Manar Ibrahim Hosny, Riyadh (SA); Sarab Abdulwahab Almuhaideb, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/275,248

(22) Filed: Jul. 21, 2025

Related U.S. Application Data

(63) Continuation-in-part of application No. 18/923,509, filed on Oct. 22, 2024.

(51) Int. Cl.
| | |
|---|---|
| *G06Q 10/0832* | (2023.01) |
| *G16H 40/20* | (2018.01) |

(52) U.S. Cl.
CPC ......... *G06Q 10/0832* (2013.01); *G16H 40/20* (2018.01)

(58) Field of Classification Search
None
See application file for complete search history.

(56) References Cited

U.S. PATENT DOCUMENTS

| | | | |
|---|---|---|---|
| 11,164,464 B1 | 11/2021 | Marriott et al. | |
| 2020/0242548 A1* | 7/2020 | Curry ................. | G07C 9/00563 |

(Continued)

FOREIGN PATENT DOCUMENTS

| | | |
|---|---|---|
| AU | 2021100672 A4 | 5/2021 |
| CN | 113345569 B | 11/2022 |

(Continued)

OTHER PUBLICATIONS

Muhammad, A., et al. Potential applications of unmanned ground and aerial vehicles to mitigate challenges of transport and logistics-related critical success factors in the humanitarian supply chain. Asian Journal of Sustainability and Social Responsibility, 5 (1) doi: 10.1186/s41180-020-0033-7. (Year: 2020).*

(Continued)

*Primary Examiner* — Emily Huynh

(74) *Attorney, Agent, or Firm* — Nath, Goldberg & Meyer; Joshua B. Goldberg

(57) ABSTRACT

A method for delivering medication or medical supplies to persons in need thereof by using drones includes receiving patient data, said data listing a plurality of patients needing medical assistance. Drone data is received, listing a plurality of drones usable to deliver medical supplies to the plurality of patients. Facility data is received, listing one or more facilities located in an area capable of providing medical assistance to the plurality of patients, and indicating which facility can be used as a drone launching center. The method includes selecting one or more facilities to be used to provide medical assistance to the plurality of patients, said selected facilities will be used as drone launching centers to provide medical assistance to the plurality of patients via the plurality of drones. Patients are assigned to each facility, drones are assigned to the selected facilities, and the patients are assigned to the drones.

6 Claims, 10 Drawing Sheets

(56) References Cited

U.S. PATENT DOCUMENTS

| | | |
|---|---|---|
| 2023/0402173 A1 | 12/2023 | Lee et al. |
| 2023/0418313 A1* | 12/2023 | Ciliberti ................... B64D 1/22 |
| 2024/0037487 A1* | 2/2024 | Clise ....................... B64D 1/12 |

FOREIGN PATENT DOCUMENTS

| | | | |
|---|---|---|---|
| IN | 202211029299 A | 12/2023 | |
| WO | WO-2019152515 A1 * | 8/2019 | ........... B64C 39/024 |

OTHER PUBLICATIONS

Al-Rabiaah, S., Hosny, M., & AlMuhaideb, S. (2022). An Efficient Greedy Randomized Heuristic for the Maximum Coverage Facility Location Problem with Drones in Healthcare. Applied Sciences, 12(3), 1403. https://doi.org/10.3390/app12031403 (Year: 2022).*

Al-Rabiaah, Sumayah, Manar Hosny, and Sarab AlMuhaideb. "An efficient greedy randomized heuristic for the maximum coverage facility location problem with drones in healthcare." Applied Sciences 12.3 (2022): 1403.

Al-Rabiaah, Sumayah, Manar Hosny, and Sarab AlMuhaideb. "A greedy heuristic based on optimizing battery consumption and routing distance for transporting blood using unmanned aerial vehicles." Electronics 11.20 (2022):3399.

* cited by examiner

START

S201 SELECT A NUMBER OF FACILITIES TO BE OPENED FROM THE POTENTIAL FACILITIES

S203 ASSIGN PATIENTS TO THE OPENED FACILITIES

S205 ASSIGN DRONES TO THE OPENED FACILITIES AND ASSIGN PATIENTS TO THOSE DRONES

END

S107

SYSTEM AND METHOD FOR DELIVERING MEDICATION AND MEDICAL SUPPLIES TO PERSONS IN NEED THEREOF IN RESPONSE TO A LARGE SCALE EMERGENCY SCENARIO

CROSS-REFERENCE TO RELATED APPLICATION

This continuation-in-part application claims priority under 35 U.S.C. § 120 to U.S. patent application Ser. No. 18/923,509, filed on Oct. 22, 2024 in the U.S.P.T.O., the disclosure of which is incorporated by reference herein in its entirety.

TECHNICAL FIELD

The present disclosure relates to a medical emergency response system, and more particularly, to a system and method for delivering medication and medical supplies to persons in need thereof in response to a large scale emergency scenario.

DISCUSSION OF THE RELATED ART

Methods of sending medical aid to persons in need by using unmanned aerial vehicles (UAVs) are known. Generally speaking, these methods include loading a UAV with medication or medical supplies (collectively referred to as "medication" for brevity purposes) and flying the UAV to the recipient's location. In cases where the number of patients in need of medication at a given time is low (e.g., one emergency at a time), a UAV can be manually operated to deliver the medication to the person in need thereof.

However, in situations where large crowds of persons gather together in a particular area, including, for example, the Hajj pilgrimage to Mecca, Saudi Arabia (where the attendance was roughly 2.5 million individuals per year prior to COVID-19), the occurrence of an unanticipated natural disaster, adverse weather event, construction accident, or other unexpected adverse event can create a large scale emergency due to the large number of persons that can be impacted (e.g., injured).

Manual UAV operation for sending medication to each person in need at the location of the person (which may be remote) is simply not practical. This is due to the large number of calculations that must be performed to determine which UAV to send to which patient, whether a particular UAV can carry the weight of the medication required by the patient, whether the UAV has the sufficient battery capacity to deliver the medication to the patient and return to its launch pad, etc.

Therefore, the assistance of a computer is required in determining how to use numerous UAVs to deliver medication to patients during large scale emergencies. Mathematical optimization, performed by employing a computer, can be used to determine which UAVs to allocate to which patient while ensuring that the UAVs are capable of delivering the payload (e.g., medication). More specifically, this type of optimization problem is considered an NP-hard problem. This means that there is no known algorithm that can solve all instances of the problem quickly (in polynomial time). Instead, solving a NP-hard problem typically requires exponential time in the worst case scenario. Therefore, the time it takes to solve a problem to an emergency scenario grows rapidly as the size of the problem increases (e.g., as the number of patients and/or number of locations where the patients are located increases).

In other words, the process of determining a solution to the problem of which UAV to allocate to which patient in a large scale emergency scenario is computationally intensive. This process consumes a large amount of electrical power and takes a long amount of time to produce a reasonable solution. Therefore, a system and method that can reduce the computational time for finding a reasonable solution to the process of assigning UAVs to patients in need of medication is needed.

SUMMARY

The present disclosure relates to a system and method for allocating UAVs to persons in need of medication during a large scale emergency event. The UAVs can then be used to deliver the medication to the recipients based on the allocation scheme.

The present subject matter improves computer technology by reducing the number of calculations that must be performed to find a reasonable solution to the NP-hard problem of allocating a large number of UAVs to a large number of persons in need of medical assistance. The reduction in the number of calculations reduces the amount of electrical power that the computer will consume by virtue of reducing the number of instructions that the central processing unit of the computer must execute. In addition, the reduction in the number of calculations also reduces the number of read and write operations to the computer's memory to store the results of the calculations. This configuration, in turn, reduces the total amount of energy used to perform the calculations.

The present disclosure also reduces the amount of time that a computer must operate to find a solution to the NP-hard problem of allocating a large number of UAVs to a large number of persons in need of medical assistance. This occurs due to the reduction in the number of calculations that must be performed to find a reasonable solution to the problem.

Accordingly, the present subject matter can be utilized to quickly and efficiently find a solution to the problem of sending medical aid to persons in need during a large scale emergency scenario by using UAVs. As a result, the persons in need can receive medical attention quickly.

BRIEF DESCRIPTION OF THE DRAWINGS

The above and other features of the present disclosure will become more apparent by describing in detail exemplary embodiments thereof in conjunction with the accompanying drawings, in which.

DETAILED DESCRIPTION OF THE EMBODIMENTS

Figure 1:
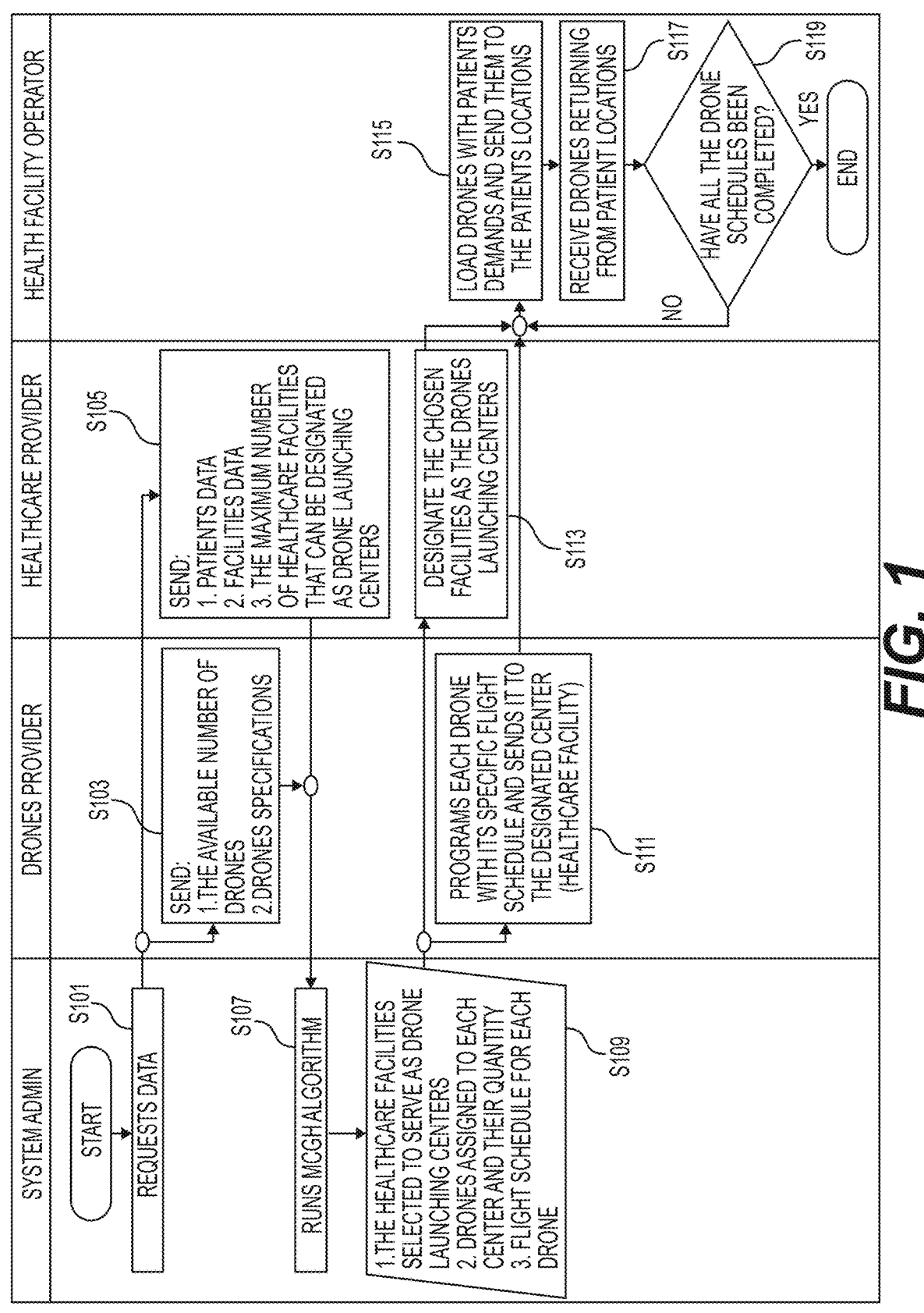
FIG. 1 is a flowchart illustrating steps for performing a method according to an exemplary embodiment of the present disclosure.

Exemplary embodiments of the present disclosure will be described more fully hereinafter with reference to the accompanying drawings. The present disclosure may, however, be embodied in different forms and should not be construed as being limited to the embodiments set forth herein. Like reference numerals may refer to like elements throughout the specification. The sizes and/or proportions of the elements illustrated in the drawings may be exaggerated for clarity.

When an element is referred to as being disposed on another element, intervening elements may be disposed therebetween. In addition, elements, components, parts, etc., not described in detail with respect to a certain figure or embodiment may be assumed to be similar to or the same as corresponding elements, components, parts, etc., described in other parts of the specification.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" may include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

The present disclosure relates to solving a Maximum Coverage Facility Location Problem with Drones (MCFLPD), a variant of an NP-hard facility location problem, to determine which healthcare facilities to be used in a large scale emergency situation, from among a total number of healthcare facilities available in a given area, to determine which patients (or persons in need of medical assistance) to assign to the facilities to be used, to assign UAVs (or drones) to the facilities to be used, and to assign the patients to the drones in a way that maximizes the objective function of serving as many individuals as possible.

The present subject matter solves the MCFLPD problem by utilizing a Maximum Coverage Greedy Heuristic (MCGH). The MCGH is a heuristic that involves greedily selecting healthcare facilities with the highest patient-serving capacity, assigning patients to the nearest open facilities, and optimizing drone-patient assignments in a way that minimizes the consumption of the battery of the drones during the trips between the patients and the facilities. Extensive experimental testing of the MCGH on generated datasets show that the MCGH significantly improves the effectiveness of solving the MCFLPD by ensuring a higher patient coverage in less time than alternative methods (and especially so for providing healthcare coverage in densely crowded gatherings).

More particularly, the MCFLPD involves two sub-problems:

(1) The facility location problem, where the total number of possible solutions can be estimated as:

$$\sum_{k=1}^{p} \binom{f}{k},$$

where f is the number of all facility locations, p is the number of the selected facility locations, and k is a counter of the selected facilities.

(2) A routing problem, where a solution is a permutation, so the total number of possible solutions can be estimated as: n!, where n is the number of locations of the patients (each patient to be visited is associated with his/her/their own location).

However, one must note that not all solutions to the MCFLPD problem are feasible or optimal. Many solutions may violate constraints or result in fewer patients served. Finding the optimal solution to the MCFLPD problem involves evaluating each possible solution to its two sub-problems and selecting the solution that maximizes the objective function of serving as many individuals as possible in a reasonable amount of time. The challenge lies in efficiently exploring this vast solution space to find the best solution within a reasonable amount of time. The MCGH, as described in the specification, can be used to explore the large number of solutions that result from solving sub-problems (1) and (2) above, to serve as many individuals as possible in a reasonable amount of time.

Therefore, the utilization of the MCGH, according to the present subject matter, can be utilized to reduce the amount of electrical power consumed by a computer during the process of determining a solution to the NP-hard problem of utilizing a given number of UAVs in a way that serves as many individuals as possible in a reasonable amount of time based on the number of local facilities that can provide medication deliverable by the UAVs to the individuals in need thereof.

FIG. 1 is a diagram illustrating a flowchart with steps for performing a method according to an exemplary embodiment of the present disclosure.

Referring to FIG. 1, step S101 includes requesting data from a provider of UAVs (e.g., a drone provider) and requesting data from a healthcare provider. The data may be requested, for example, by an administrator capable of performing the MCGH method.

Step S101 may include requesting the number of persons in need of medical assistance in a particular area (e.g., a town, a county, a village, a particular region of land and/or water, etc.), the type of medical assistance needed by each person, the location of each person, and identifying information about each person needing medical assistance (e.g., each person's name, age, gender, etc.). This information can be requested, for example, from a healthcare provider. The healthcare provider can be a governmental entity or other entity entrusted with keeping track of the health condition of individuals in the region.

Step S101 also includes requesting a number of available healthcare facilities that can potentially be used to provide medical assistance to the persons in need thereof, the type of medical assistance that can be provided by each healthcare facility (including the types of medication and/or medical supplies stocked by the facility along with their quantity and weight), the schedule of medical staff for each healthcare facility, etc. This information can also be requested, for example, from the healthcare provider.

In addition, step S101 includes requesting a number of available drones that can be used to deliver medical supplies to the persons in need thereof, along with the technical specifications of the drones. This information can be requested, for example, from a drone provider.

While the requests for information of step S101 are indicated above as being directed to a drone provider and to a healthcare provider, the requests can be made to any entity capable of providing answers to the requests made, including providing the drones for delivering medical supplies to the persons in need thereof. However, the requests for information will be described in this specification as being made to the drone provider and to the healthcare provider for convenience of explanation.

Referring to FIG. 1, step S103 includes receiving drone data from the drone provider in response to the request made in step S101. The drone data includes how many drones are available (e.g., one or more drones) for utilization in the particular given area to deliver medical supplies to persons in need thereof (which may alternatively be referred to as patient(s)) in case of an emergency.

Step S103 may also include receiving technical specifications of each available drone. For each drone, the technical specifications may include, for example, the lift-to-drag ratio, the battery capacity, the battery mass, the mass of the drone without the battery and load, the efficiency of the power transfer, the weight of a payload (e.g., medication) that the drone can transport, etc. A drone identification number (ID) may be assigned to each drone for identification purposes.

Referring to FIG. 1, step S105 includes receiving data from the healthcare provider in response to the request made in step S101. The data received in step S105 includes patient data, facility data, and the maximum number of facilities that can be designated (or used) as drone launching centers for launching the drones loaded with medication for the patients.

The healthcare provider can be, for example, an entity that monitors, supervises and/or controls healthcare facilities (e.g., hospitals, ambulatory centers, or more generally, a facility capable of providing medical assistance to a patient) in the same area where the drones can be used.

The patient data received in step S105 may include the number of patients (e.g., one or more patients) needing medical help in the area capable of being served by the drones, each patient's location, a description of each patient's symptoms and/or type of medical assistance needed, and each patient's information, such as name, address, age, gender, etc.

Based on the description of the symptoms and/or type of medical assistance needed for each person, the weight of medical supplies and/or medication needed to be delivered to each patient to address the patient's medical needs can be determined (along with a description of the type of medication and/or medical supplies). The weight of medical supplies and/or medication needed to be delivered to a patient can alternatively be referred to as weight demand or weight demand of medication.

The facility data received in step S105 may include the number of facilities (e.g., one or more facilities) located in the area capable of being served by the drones and/or capable of providing medical assistance to the patients listed in the patient data. For each facility, the facility data may include the facility's location, name, type of facility (e.g., a hospital, an ambulatory center, an urgent care facility, etc.), a listing of medication and medical supplies stocked by the facility along with their quantity (the quantity lists the weight of each medication and/or medical supply item), the types of medical procedures/services that can be performed, an up to date list of the equipment available in the facility, the availability of staff, etc. Each facility may be associated with a facility ID number for identification purposes.

Not every facility in a given area may be adapted for launching drones. This may be, for example, due to zoning regulations restricting usage of drones over and around a facility, the lack of a suitable area for launching drones, lack of staff trained to launch and service drones, etc. For this reason, step S105 includes an indication of the maximum number of facilities that can be used for launching drones along with their respective facility ID numbers.

Referring to FIG. 1, step S107 includes running an algorithm of the MCGH method (or performing the MCGH method of the present disclosure) based on the input received from steps S103 and S105. Step S107 will be described below in detail.

As indicated in step S109, the performance of step S107 can resulting in determining the number of healthcare facilities that will serve as drone launching centers along with presenting the facility ID number of each said facility. Step S109 also includes determining the number of drones (with their accompanying ID numbers) to be used in each facility that will serve as a drone launching center. In addition, step S109 includes determining (or delineating) a flight schedule for each drone in each facility that will serve as a drone launching center.

Step S111 includes programming each drone with its flight schedule (e.g., flight path instructions), and sending each programmed drone to the facility designated to serve as its drone launching center.

Step S113 includes designating the chosen facilities as drone launching centers.

Step S115 includes loading the drones at each facility designated to serve as a drone launching center with a package containing the medication needed by the intended recipient (or patient) and sending (or flying) the drones to the patient locations (e.g., to the patients).

Step S117 includes receiving the drones returning from the patient locations.

When not all of the drones' schedules have been completed (at each drone launching facility), (Step S119), the method reverts to step S115. Each drone's schedule has been completed when the drone is assigned a patient, is loaded up with supplies (i.e., the package containing the medication needed by the intended recipient), delivers the supplies, and returns to the facility (e.g., the facility it was launched from or to another facility from among the list of drone launching centers).

When each drone's schedule has been completed for all of the drones (and/or each drone has completed all of its missions (or trips) if a drone is schedule to deliver medication to one or more patients via one or more trips), (step S119), then the method is ended.

Step S107 will now be described in detail with reference to FIG. 2.

As indicated in this specification, step S107 includes receiving as input the data received in steps S103 and S105.

The performance of step S107 will also be made with reference to Table 1 below. Table 1 lists the formulation of the MCFLPD. The MCFLPD includes sets, parameters, decision variables, the objective function, constraints, and assumptions for the method of step S107.

TABLE 1

| Formulation of the MCFLPD | | |
|---|---|---|
| Sets | I: Set of locations of patients (i ∈ I) | |
| | J: Set of all possible facility locations (j ∈ J) | |
| | K: Set of drones (k ∈ K) | |
| Parameters | $\eta$: Efficiency of the power transfer | |
| | $\theta_s$: Lift-to-drag ratio | |
| | B: Drone battery capacity | |
| | $b_{ij}$: Battery consumed on one trip between patient i ∈ I and facility j ∈ J | |
| | $d_{ij}$: Travel distance between patient i ∈ I and facility j ∈ J | |
| | $\mu_b$: Drone battery mass | |
| | $\mu_t$: Drone mass tare, without battery and load | |
| | p: Maximum number of facilities to be opened | |
| | c: Capacity of each opened facility | |
| | $w_i$: Weight of demand at patient location i ∈ I | |
| Decision Variables | $x_{ijk} = \begin{cases} 1 & \text{if patient i is served by the } k^{th} \text{ drone of facility } j \in J \\ 0 & \text{otherwise} \end{cases}$ | (1) |
| | $y_j = \begin{cases} 1 & \text{if a facility is opened at } j \in J \\ 0 & \text{otherwise} \end{cases}$ | (2) |
| | $z_{jk} = \begin{cases} 1 & \text{if a drone } k \text{ is assigned to facility } j \in J \\ 0 & \text{otherwise} \end{cases}$ | (3) |
| | $l_{ij} = \begin{cases} 1 & \text{if patient i is a potential patient at facility } j \in J \text{ where } b_{ij} < B \\ 0 & \text{otherwise} \end{cases}$ | (4) |
| | $a_{ij} = \begin{cases} 1 & \text{if patient i is assigned to facility } j \in J \\ 0 & \text{otherwise} \end{cases}$ | (5) |
| Objective Function | Maximize $\sum_{i \in I} \sum_{j \in J} \sum_{k \in K} w_i x_{ijk}$ | (6) |
| Constraints | $\sum_{j \in J} \sum_{k \in K} x_{ijk} \leq 1, \forall i \in I$ | (7) |
| | $\sum_{j \in J} y_j \leq p$ | (8) |
| | $\sum_{i \in I} b_{ij} x_{ijk} \leq B z_{jk}, \forall j \in J, k \in K$ | (9) |
| | $\sum_{i \in I} \sum_{k \in K} w_i x_{ijk} \leq c y_j, \forall j \in J$ | (10) |
| | $z_{jk} \leq y_j, \forall j \in J, k \in K$ | (11) |

TABLE 1-continued

Formulation of the MCFLPD $$\sum_{j \in J} z_{jk} \leq 1, \forall\, k \in K \tag{12}$$

$$x_{ijk}, y_j, z_{jk} \in \{0, 1\}, \forall\, i \in I, j \in J, k \in K \tag{13}$$

| Assumptions | 1. | If the weight demand of a patient is higher than the carrying capacity of the drone, multiple trips will be conducted to meet the patient's needs; in this case, the number of trips will be based on drone capacity. |
|---|---|---|
| | 2. | Each drone can complete several one-to-one trips (where a trip lasts from drone launching center to a patient's location and back) until the battery range B is met. |
| | 3. | Recharging of drone batteries is not considered (i.e., it is assumed that the drone batteries are fully charged prior to the start of a trip). |
| | 4. | The effects of weather and charging cycles on drone battery capacity are not considered. |
| | 5. | The effect of obstacles, such as high buildings or mountains, on drone battery capacity is not considered. |
| | 6. | The total power consumed $b_{ij}$ in a delivery from facility j to patient i is given by Equation (14). $\mu_r$, $\mu_b$, $\theta_s$, and $\eta$ are fixed for all UAVs, so we treat them as constants. |
| | 7. | The capacity of each opened facility is calculated by Equation (15). |

The MCFLPD is an NP-hard combination optimization problem. The solutions in combination optimization problems are encoded with discrete variables. The MCFLPD was formulated as follows: within a certain planning period, there is a set of locations for patients I, where each has a demand weight $w_i$, along with a set of potential facility locations (i.e., drone launching centers) J and a set of drones K, each with a full battery charge.

The demand weight w; is the weight of medical supplies and/or medication needed to be delivered to a patient to address the patient's medical need.

There are five decision variables of the Boolean type: $x_{ijk}$ (1), $y_{ik}$ (2), $z_{jk}$ (3), $l_{ij}$ (4), and $a_{ij}$ (5) (i.e., see decision variable (5) in Table 1 above. Reference numerals in parenthesis below correlate to the equation numbers in Table 1 above. The objective (6) is to maximize the ability of the fleet of drones to cover the total patient demand. Constraint (7) ensures that each patient location is covered at most once. Constraint (8) guarantees that the number of chosen facilities must be less than or equal to the maximum number of existing facilities. Constraint (9) ensures that the drone battery range must cover the trip distance. Constraint (10) guarantees that the patient demand served by each selected facility must be less than or equal to the facility's capacity. Constraint (11) enforces drones to be assigned to only the located facilities. Constraint (12) enforces that each drone is assigned to at most one open facility. Constraint (13) relates to the specifications of the decision variables, mandating that they must all be binary. Equation (14) below calculates by i.e., the total power consumed in a delivery from facility j to patient i, where a drone travels to patient i with a load $w_i$ and drops $w_i$ then returns empty to the facility j.

$$b_{ji} = \frac{m_t + m_b + w_i}{\theta_s \eta} d_{ij} + \frac{m_t + m_b}{\theta_s \eta} d_{ij} \forall\, i \in I, j \in J \tag{14}$$

As indicated above, equation (14) is calculated for each facility $j \in J$. The distance between each facility and each patient is calculated using the following equation:

$$Distance = \sqrt{\begin{array}{l}((facilityLatitude - patientLatitude) * degreeOfLatitude)^2) + \\ ((facilityLongitude) * degreeOfLongitude)^2)\end{array}}$$

The distance can then be converted into miles. The following apply to equation (14):

$\eta$: Efficiency of the power transfer $\theta_s$: Lift-to-drag ratio

B: Drone battery capacity $b_{ij}$: Battery consumed on one trip between patient $i \in I$ and facility j & J $d_{ij}$: Travel distance between patient $i \in I$ and facility $j \in J$ $m_b$: Drone battery mass $m_t$: Drone mass tare, without battery and load $w_i$: Weight of demand at patient location $i \in I$ Equation (15) calculates c, i.e., the capacity of each opened facility which is equal to the total demand weights of all patients divided by 0.8 percent of the number of facilities to be opened. Generally speaking, the average utilization of the facilities is equal to 80 percent of the total available capacity.

$$c = \frac{\sum_{i \in I} w_i}{0.8p} \tag{15}$$

Figure 2:
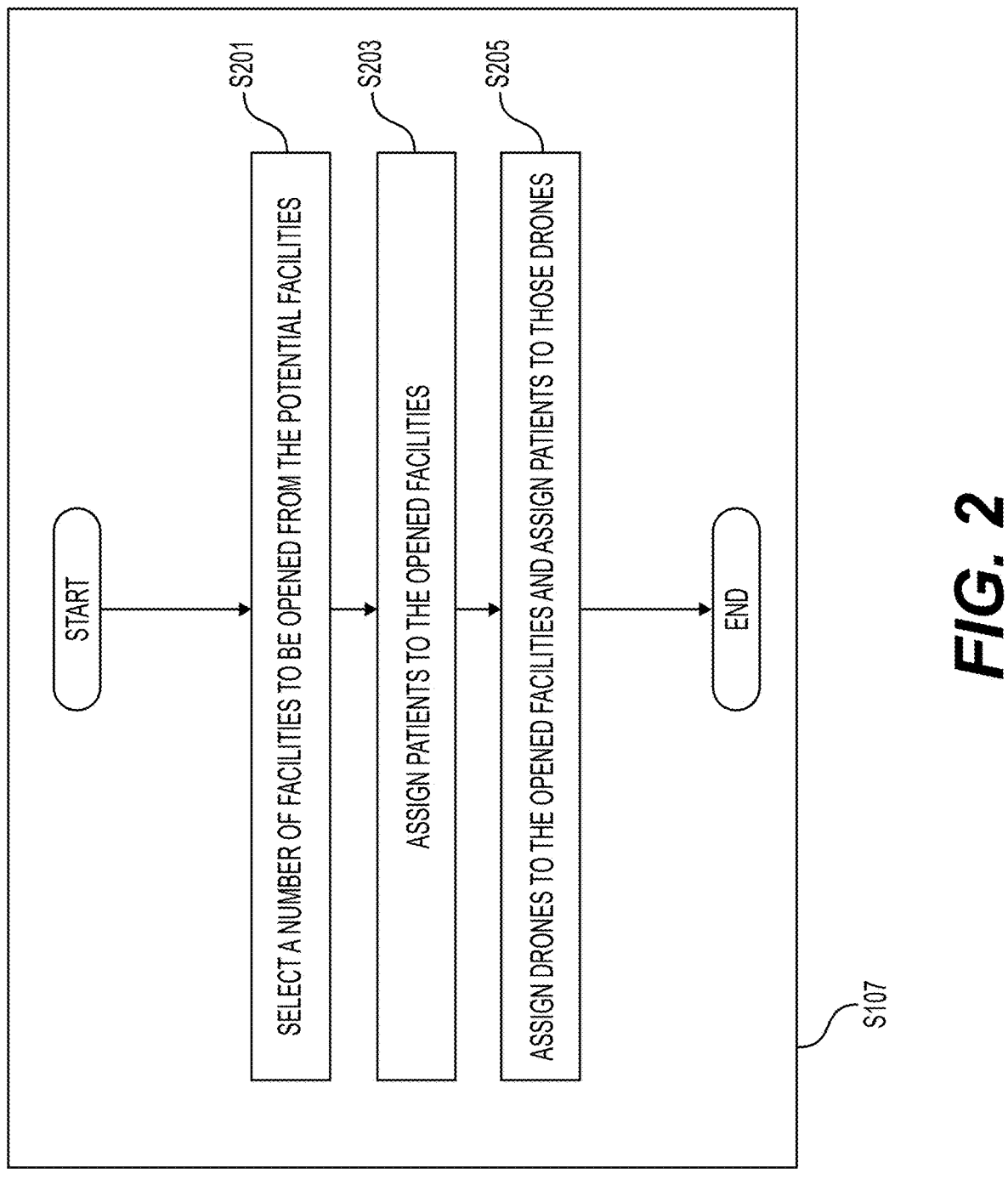
FIG. 2 is a flowchart illustrating sub-steps of a method step included in the method of FIG. 1.

Referring now to step S201 in FIG. 2, the performance of the MCGH algorithm includes selecting a number of facilities to be opened from the list of potential facilities. In other words, step S201 includes determining which facilities will be used as drone launching centers (or drone launching facilities) from among the list of facilities received from the healthcare provider in step S105.

Figure 3A:
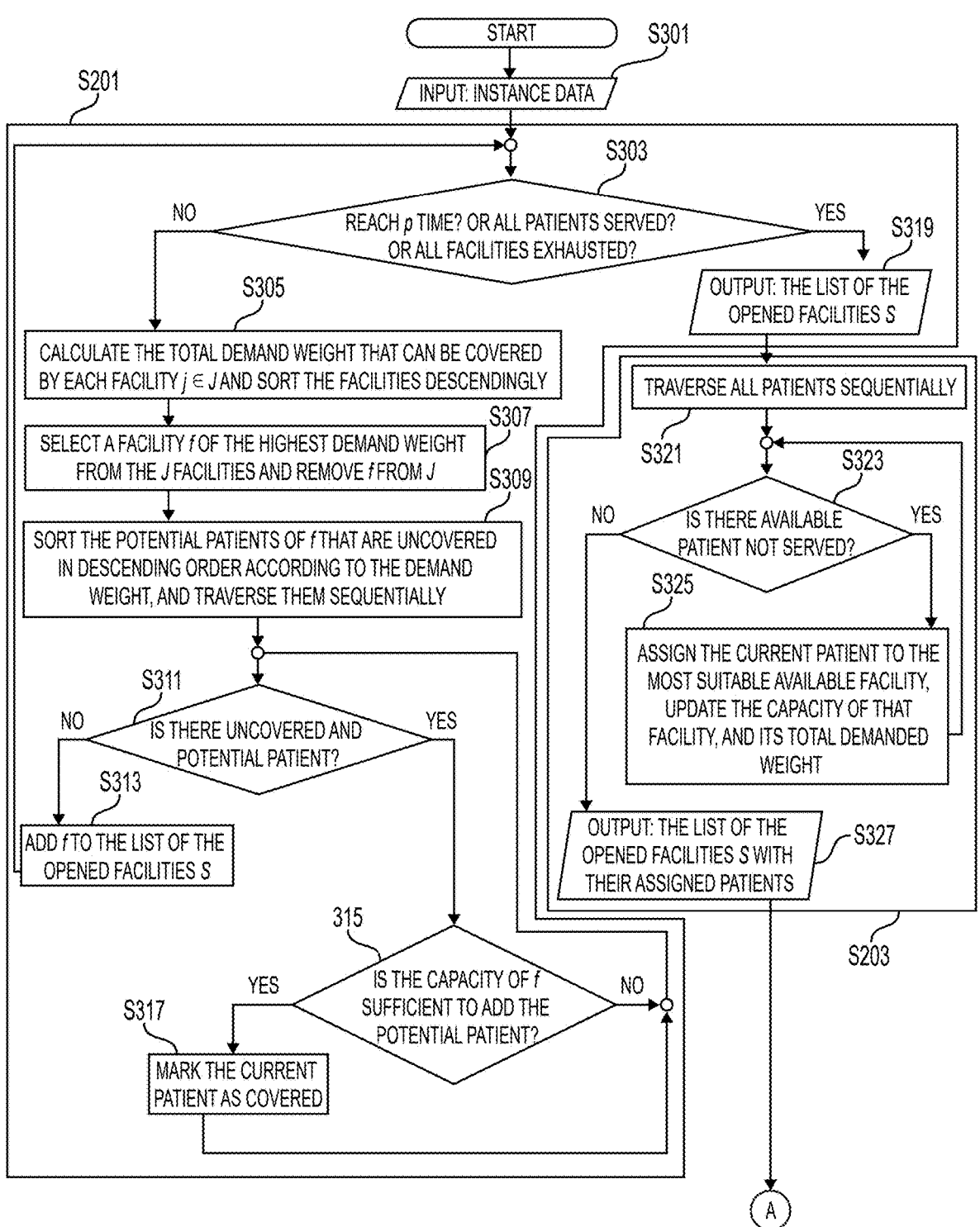
FIGS. 3A and 3B are a flowchart illustrating sub-steps of the sub-steps illustrated in FIG. 2.
Figure 3B:
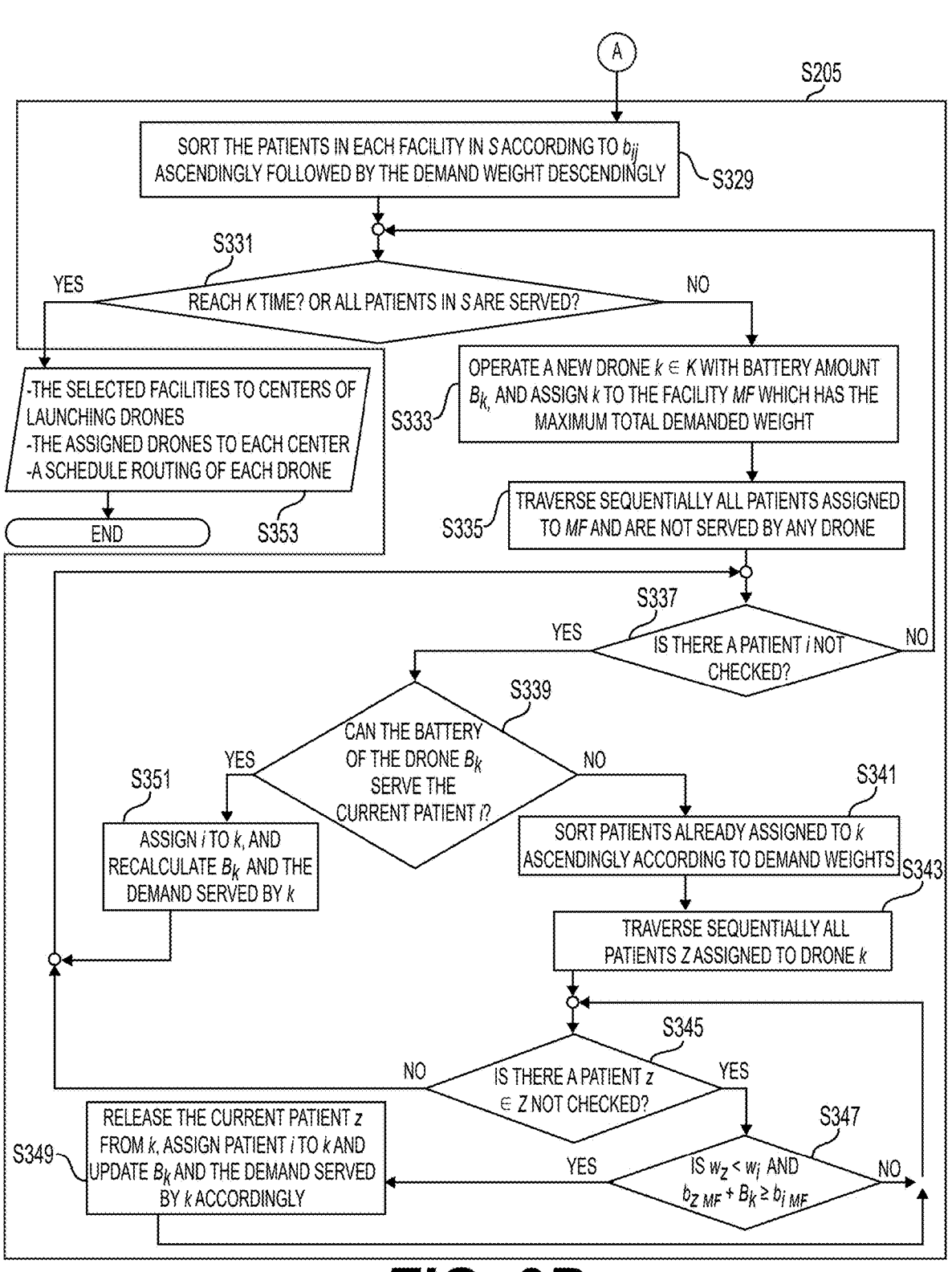

FIG. 2 illustrates the three main sub-steps S201, S203 and S205 of the MCGH heuristic of the present disclosure. FIGS. 3A and 3B illustrate a detailed flowchart of the method of performing sub-steps S201, S203 and S205.

Referring now to FIG. 2, the concept behind the method of sub-steps S201-S205 is to select a set of facilities S to be opened (step S201), with size p, from the set of potential facilities J that maximizes $\Sigma_{i \in I} \Sigma_{j \in S} y_j l_{ij} w_i$ (i.e., maximizing the total demand of patients that can be served). In turn, the algorithm assigns each potential patient to the nearest open facility $j \in S$ with the available capacity $c_j$ (step S203). Any available drones are then assigned to the opened facilities according to the highest unserved demand weights $\Sigma_{i \in I} w_i d_{ij}$, where $a_{ij}=1$ and $j \in S$. Finally, patients are assigned to drones (in each opened facility) according to the lowest battery consumed $b_{ij}$ followed by the highest demand weight $w_i$ of all unserved patients of a specific facility j, such that for each drone k, the total battery consumed by the drone in serving the demand is less than the drone's total battery capacity that is, $\Sigma_{i \in I} b_{ij} \leq B_k$, where $j \in S$ (step S205).

Step S201, which may also be alternatively referred to as "Algorithm 1", is configured to select facilities to be opened in a greedy manner, i.e., the facilities that can serve the largest total demand weights of potential patients.

Referring to FIGS. 3A-3B, step S301 includes taking as input the data received from steps S103 and S105.

Step S201 then includes using the data received from step S301 to select from potential facilities J a number of facilities p to be opened (e.g., to be used as drone launching centers) that maximizes the total demand of patients that can be served. Only facilities J that can serve as drone launching centers are considered. Facilities from which drones cannot be launched are not considered. With reference to the table named "Algorithm 1" below, let I be the list of all potential patients and J be the list of all potential facilities with their potential patients such that patient i can be covered by facility j if a drone can reach i in one trip using its battery charge. In other words, $b_{ij} \leq B$, where $b_{ij}$ is calculated using equation (14). In addition, suppose that p is the maximum number of facilities to be opened. Let S be an empty list of the initial solution of size p to maintain open facilities. Let $c_f$ be the capacity of each facility calculated according to equation (15) (e.g., all facilities have identical capacities).

Algorithm 1 repeats the following steps p times, until J is exhausted or until all patients in I have been served: First, calculate $\Sigma_{i \in I} w_i l_{ij} \forall j \in J$ (step S305). That is, calculate the total demand weight (of medical supplies and/or medication) that each facility can provide for the potential patients for each facility $j \in J$. In turn, J is sorted in descending order according to these values. Then, select a facility with the highest $\Sigma_{i \in I} w_i l_{ij}$ (step S307). That is, select the facility that can supply the highest total demand weight.

In this case, a greedy selection approach is used to ensure that the selected facility can cover a large patient demand and complete the calculation process in a short amount of time and in one run. This method of operation is more efficient than other methods known in the art (including a maximum coverage greedy randomized heuristic (MCGRH) approach) because the present disclosure requires the calculation process (of selecting a facility that can cover a large patient demand) to be completed in one run. The completion of the calculation process in one run is quick and consumes little energy since the computer performs the calculation only once. The MCGRH approach, on the other hand, must run the calculation of selecting a facility multiple times to select the best result. This is because the MCGRH approach is a random heuristic. Algorithm 1 of the present subject matter (MCGH) is not random. The performance of the calculation multiple times in the MCGRH approach consumes more time and more electricity by virtue of utilizing a computer for a longer period of time to complete the calculation.

Therefore, the present subject matter can be used to solve the problem of selecting the number of facilities to be used as drone launching centers more efficiently, rapidly, and by utilizing less energy than known approaches while ensuring that the selected facilities that can serve the largest total demand weights of potential patients. The results of an exemplary run of the MCGH heuristic are demonstrated in Table 5 below.

Next, and with reference to FIGS. 3A-3B, f is removed from J so that it will not appear again in subsequent iterations when selecting a new facility to be opened (step S307). That is, the selected facility that can supply the highest total demand weight, from among the list of facilities that can serve as drone launching centers: (1) is marked as a facility that will be used for providing medical assistance to patients (e.g., to be used as a drone launching center), and (2) the patients that the marked facility can supply with medication or medical supplies are marked as covered. Therefore, the marked facility is removed from the list of facilities to be considered as being used as drone launching centers in a subsequent iteration, and the marked patients are removed from the pool of patients whose medical weight demands need to be covered in a subsequent iteration.

Referring to FIGS. 3A-3B, the potential patients i of f, where $i \in I$ and $l_{ij}=1$, are sorted in descending order according to the demand weight $w_i$ (step S309). Following this, iterate over these patients and mark them as covered until $c_f$ is filled (steps S311, S313, S315 and S317), or until the list of f's potential patients is exhausted (S303), thus making these patients unavailable for other facilities.

Hence, if there is more than one facility in J with the same potential patient A, marking A as covered by f will change $\Sigma_{i \in I} w_i l_{ij} \forall j \in J$ (i.e., the total demand weights of the potential patients of each facility $j \in J$). It is noteworthy that this affects their appearance in the next iteration. The last part of the second algorithm adds f to S (step S313).

Then, list S now contains the facilities to be opened that can serve the greatest possible demands (S319).

As can be understood based on the description of steps S303-S319, the performance of said steps can result in selecting one or more facilities to be used as a drone launching center and to cover at least one patient for each facility selected to be used as a drone launching center.

TABLE 2

| Algorithm 1: MCGH: Select a number of facilities to be opened from the potential facilities. |
| --- |
| 1. I ← List of all potential patients |
| 2. J ← List of all potential facilities with their potential patients |
| 3. p ← Maximum number of facilities to be opened |
| 4. S ← { } |
| 5. Calculate $c_f = \dfrac{\sum_{i \in I} w_i}{0.8\, p}$ // capacity of each facility $f \in S$ |
| 6. Repeat |

TABLE 2-continued

Algorithm 1: MCGH: Select a number of facilities to be opened from the potential facilities.

7.    Calculate $\Sigma_{i \in j} w_i l_{ij}$ $\forall j \in J$ // the total demand weights of the potential patients of each
      facility $j \in J$
8.    Sort(J) // in descending order of the total demand weights of the potential patients
9.    f ]← J[1]
10.   Remove (f,J)
11.   Sort(potiential patients of f) // in descending order of patients demand weight $w_i$
12.   Repeat
13.      MarkAsCoverd (patient$_i$, f)
14.   Until filling $c_f$ OR the list of f's potential patients is exhausted
15.      S ← S ∪ f
16. Until Size p is reached OR I is exhausted OR J is exhausted
17. Output: S Step S203 may be performed subsequent to step S201. Step S203 may also be alternatively referred to as "Algorithm 2".

The purpose of Algorithm 2 is to assign patients to the nearest open facility in S that can available capacity and to satisfy the drone constraints. In step S, 203, and using S from Algorithm 1 as an input list of opened facilities with size p, along with the list of all potential patients I, several operations should be performed. First, and with reference to FIGS. 3A-3B, for each patient i in I, traverse the patients one by one until the list of patients ends (step S321), such that the current patient i is assigned to the first open facility f in the list S based on two conditions: (i) f is the nearest opened facility to i, where $b_{if} \leq B$; and (ii) there is available capacity in f to add i (i.e., $w_i \leq U_f$) (step S323). The second operation recalculates $U_f$ (i.e., the available capacity) and $\Sigma_{i \in I} w_i a_{if}$ (total demand served by f) (step S325). Step S327 includes outputting the list of the opened facilities S with their assigned patients to step S205.

Steps S321-S327 can be performed to assign at least one patient to each facility selected to be used as a drone launching center.

A table (Table 3) for Algorithm 2 is presented below.

TABLE 3

Algorithm 2: Assign patients to the opened facilities.

| | |
|---|---|
| 1. | Input: S \\ the list of opened facilities from Algorithm 1 |
| 2. | I ← List of all potential patients |
| 3. | For each patient i in I Do |
| 4. | Pick best f for i from S \\ the nearest opened facility where $b_{if} \leq$ B with available capacity $U_f$ |
| 5. | Assign(i,f) |
| 6. | Recalculate available capacity ($U_f$) and total required demands weights from f ($\Sigma_{i \in I} w_i a_{if}$) |
| 7. | Output: S |

Step S205 may be performed subsequent to step S203. Step S205 may also be alternatively referred to as "Algorithm 3".

The purpose of Algorithm 3 is to assign the available drones to the opened facilities in S according to the required demand weights of their assigned patients. This is achieved using the concept of the maximum-profit knapsack problem, along with additional conditions. The idea is to prioritize facilities that have large required demand weights by assigning more drones to them and, at the same time, assigning more patients of these facilities to drones to maximize coverage.

Given S, which is the input list of the opened facilities from Algorithm 2 (from step S327), for each facility f in S, in order to give priority to patients who consume lower batteries, sort the assigned patients i of f, where $i \in I$ and $a_{if} = 1$, in ascending order according to $b_{if}$ followed by $w_i$ in descending order (step S329). In other words, if two patients are equal in bis, the patient with the higher $w_i$ will occur first in the list.

Assuming K is the number of available drones and Total_demand_served (see the table for Algorithm 3 below) is initialized at a value of 0, repeat the following steps K times or until all patients in S are served (step S331):

First, select a drone k from the set of available drones K. To maximize coverage, find MF facility of S that has the maximum demand weights of the patients assigned to this facility that are not yet assigned to any drone (i.e., maximum facility MF from S according to maximum $\Sigma_{i \in I} w_i a_{if}$, where $x_{ifk} = 0$ $\forall f \in S$ and $\forall k \in K$). In turn, assign k is assigned to MF and the demand served by drone k (Demand_served$_k$) to 0 (step S333).

Second, traverse the patients assigned to MF who are not assigned to any drone (step S335), and then check whether the value of $b_{i\ MF}$ of the current patient i is lower than the remaining battery capacity $B_k$ of drone k (steps S337 and S339). If this is the case, assign i to k, subtract its consumed battery $b_{i\ MF}$ from $B_k$, and add $w_i$ to the drone's Demand_served$_k$ (step S351); otherwise, if the current patient i cannot be served by the remaining $B_K$—and to maximize the coverage, try to replace patient i with patient z already assigned to k (step S349), where $w_z < w_i$, without violating the drone constraints. This is done by sorting the patients already assigned to k according to ascending demand weights w (step S341), traversing them one by one (step S343), and checking whether there is a patient z for whom $w_z < w_i$ and $b_{z\ MF}$ + the remaining $B_k \geq b_{i\ MF}$ (steps S345 and S347). Then, release the assigned patient z and assign the current patient i to k (step S349). Also, and update Demand_served$_k$ and $B_k$ according to the changes (step S351).

Finally, after completing the assignments to drone k, we update Total_demand_served. After finishing all drones or serving all patients in S, calculate and return Coverage, which is equal to the percentage of Total_demand_served.

Steps S329-S351 can be performed to assign at least one drone, from the plurality of drones, to each facility from among the selected one or more facilities. In addition, steps S329-S351 can be performed to assign at least one patient to each drone, from among the at least one patient and the at least one drone assigned to each facility, at each one of the one or more facilities selected to be used as drone launching centers.

TABLE 4

| Algorithm 3: Assign drones to the opened facilities and assign patients to those drones. |
| --- |

1.     Input: S \\ from Algorithm 2
2.     K ← number of the available drones
3.     Total_demand_served ← 0
4.     Sort (patients in each facility f in S) \\ by $b_{if}$ in ascending order, followed by $w_i$ in descending order
5.     Repeat
6.       Select (new k ∈ K)
7.        B ←battery capacity of k
8.        MF ← Max(S) \\ according to max $\Sigma_{i \,\epsilon\, I}\, w_i\, a_{if}$ where $x_{ifk} = 0\ \forall\ f \in S$ and $\forall\ k \in K$
9.     Assign_drone(k, MF)
10.    Demand_served$_k$ ≤ 0
11.    For each patient i assigned to MF Do \\ i is not assigned to any drone ($x_{ifk} = 0\ \forall\ f \in S$ and $\forall\ k \in K$)
12.       $b_{i\,MF}$ ← battery consumed between current patient i and current facility MF
13.       IF $b_{i\,MF}$ ≤ B Then
14.         Assign_patient (i, k)
15.         B ← B – $b_{i\,MF}$
16.         Demand_served $_k$ ← Demand_served $_k$ + $w_i$
17.       Else
18.         Sort(patients assigned to k)\\ according to the ascending demands weights w
19.         For each patient z assigned to the drone k Do
20.           IF $w_z < w_i$ AND $b_{z\,MF}$ + B ≥ $b_{i\,MF}$ Then
21.            Release (z, k)
22.            Assign_patient (i, k)
23.            B ← B + $b_{z\,MF}$ – $b_{i\,MF}$
24.            Demand_served$_k$ ← Demand_served$_k$ + $w_i$ – $w_z$
25.            break
26.       Total_demand_served ← Total_demand_served + Demand_served$_k$
27.   Until K times OR until all patients in S are served
28.       Coverage ← The percentage of Total_demand_served of patients covered
29.   Output: Coverage Therefore, step S353 includes a list of the facilities selected to serve as drone launching centers, the list of drones assigned to each drone launching center (for all of the facilities selected to serve as drone launching centers) and a schedule routing (or flight schedule) of each drone in each drone launching center. The flight schedule includes each individual trip of each drone, including a departure coordinate and an arrival coordinate for each individual trip between its drone launching facility and each patient that the drone is assigned to serve (e.g., deliver medication to and/or from).

In addition, step S353 may also include the Coverage value, which is the percentage of the total demand of medication that needs to be transported between all of the selected drone launching centers and all of the patients needing medical assistance.

The performance of Algorithms 1, 2 and 3 of the present disclosure can be used to select facilities that can serve the largest total demand weights of potential patients as drone launching centers, assign the patents to the facilities, assign the drones to the selected facilities and assign the patients to the drones in a rapid and efficient manner due to performing the calculation for selecting each drone launching facility only once. This configuration reduces the amount of time needed to perform the selection and assignment processes of the present disclosure and reduces the amount of energy needed to perform the selection and assignment processes.

Figure 4:
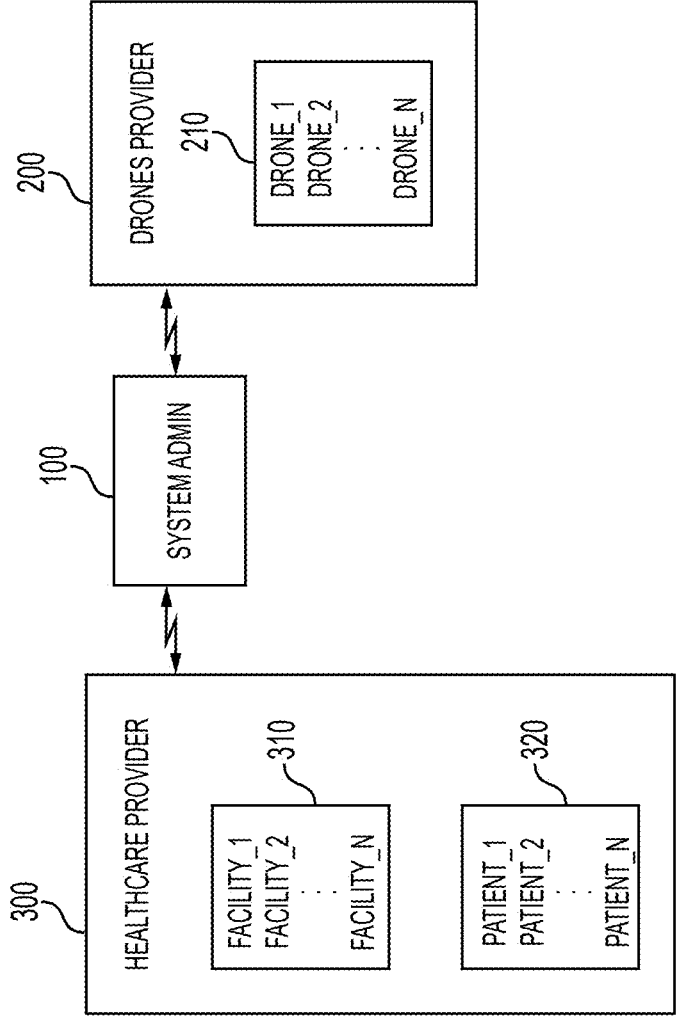
FIG. 4 is a diagram illustrating a system configured to perform the method of FIG. 1, according to an exemplary embodiment of the present disclosure.

FIG. 4 is a diagram illustrating a system of the present disclosure that utilizes the method of FIGS. 1-3 for delivering medication and medical supplies to persons in need thereof in response to a large scale emergency scenario.

Referring to FIG. 4, a system for delivering medication and medical supplies to persons in need thereof in response to a large scale emergency scenario includes a system administrator 100, a drone provider 200 communicatively coupled to the system administrator 100, and a healthcare provider communicatively coupled to the system administrator 100.

The system administrator 100 includes a computer system that comprises a processor and a non-transitory, tangible, program storage medium, readable by the computer system, embodying a program of instructions executable by the processor to perform method steps for delivering medication and medical supplies to persons in need thereof in response to a large scale emergency scenario. The computer system may be, for example, a personal computer (PC), a server, a workstation, etc.

The drone provider 200 includes a list of drones (or UAVs) 210. The list of drones 210 may include a plurality of UAVs, including drone_1 to drone_N, with "N" being a positive nonzero integer. The list of drones 210 may include the specifications for each drone as described with reference to step S103 of FIG. 1. The list of drones can be transmitted to the computer system of the system administrator 100 upon request.

The healthcare provider 300 includes a list of healthcare facilities 310 and a list of patients (or persons in need of medical assistance) 320. For example, the list of healthcare facilities 310 includes facility_1 to facility_N (as indicated elsewhere in this specification, N is a positive nonzero integer). The list of healthcare facilities 310 may include the information described with reference to step S105 of FIG. 1 for each one of the facilities included therein.

The list of patients 320 includes patient_1 to patient_N. The list of patients 320 may include the information described with reference to step S105 for each one of the patients included therein. Merely as an example, the list of patients 320 may be compiled by one or more sources that observe the effects of the emergency scenario and report their observations to the healthcare provider 300 or to another agency that then reports said information to the healthcare provider 300. Alternatively, or in addition, the list of patients 320 may be compiled by the patients themselves calling the healthcare provider 300 (or another agency that reports to the healthcare provider 300) and reporting their health condition.

Figure 5:
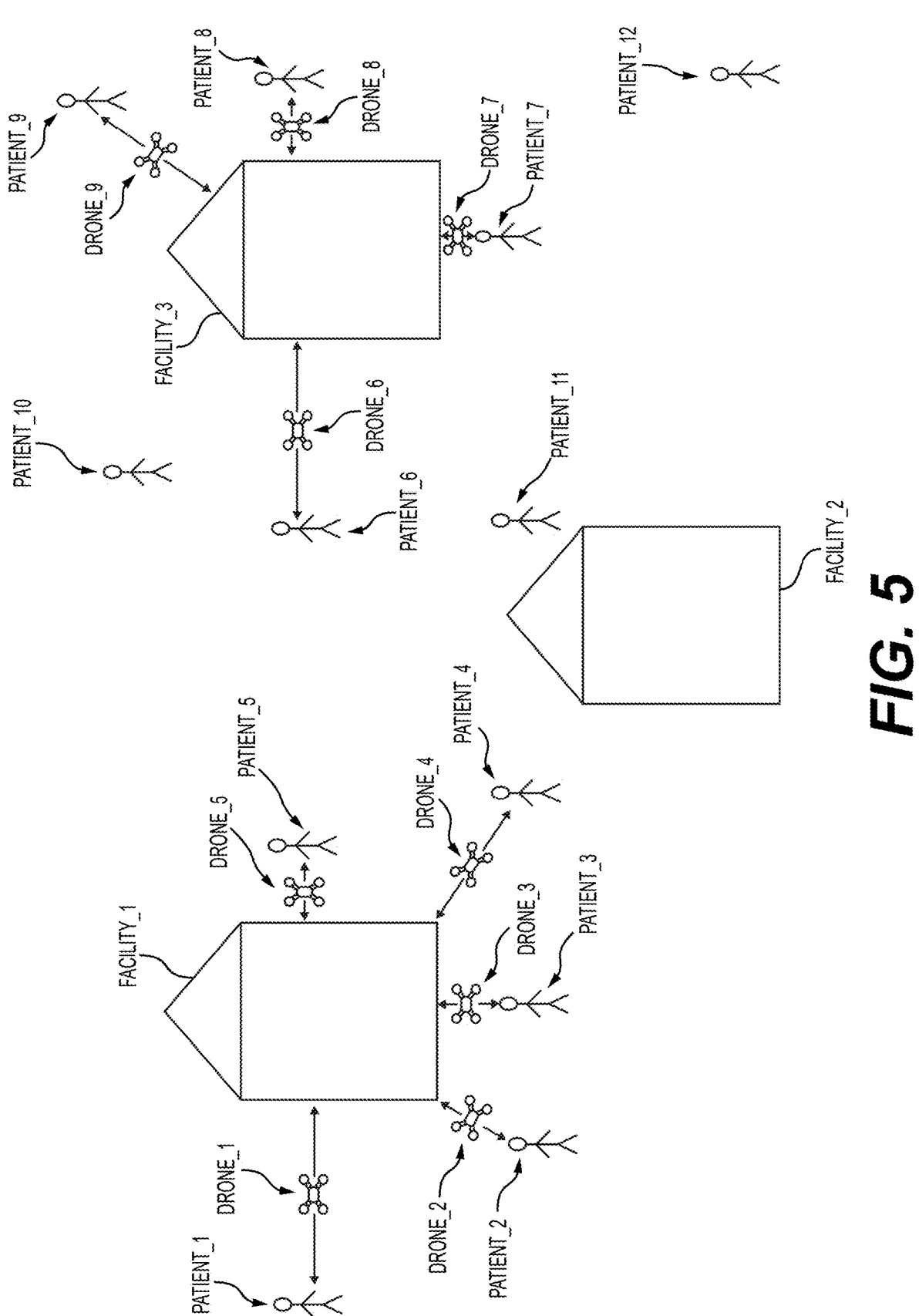
FIG. 5 is a diagram illustrating an exemplary run of the system of FIG. 4.

FIG. 5 is a diagram illustrating the results of an exemplary run of the system of FIG. 4.

The number of facilities, the number of patients and the number of drones illustrated in FIG. 5 is selected solely for illustrative purposes to provide an example of the results produced by performing the method of FIGS. 1-3 by using the system of FIG. 4. The spatial relationship between the facilities and the patients in FIG. 5 is roughly indicative of the spatial relationship between the facilities and patients for the purpose of demonstrating which patients are located closer to a facility and which patients are located farther from a facility. For example, FIG. 5 illustrates patient_6 as being located nearer to facility_3 than facility_1 or facility_2. This indicates that in real life, patient_6 is located closer to facility_3 than to facilities_1 and 2.

In the example of FIG. 5, facility_1 and facility_3 are selected to be drone launching centers. Facility_2 is not.

In the example of FIG. 5, patient_1 to patient_5 are assigned to facility_1, and patient_6 to patient_9 are assigned to facility_3. Patient_10 to patient_12 are not assigned to any facility. Therefore, patient_10, patient_11 and patient_12 will not receive medication via any of the drones of FIG. 5.

Referring to FIG. 5, the drone_1 to drone_5 are exemplarily assigned to facility_1, and drone_6 to drone_9 are exemplarily assigned to facility_3. As illustrated in FIG. 5, patient_1 to patient_5, respectively, are assigned to drones_1 to 5. Patient_6 to patient_9, respectively, are assigned to drones_6 to 9.

Table 5 below represents a comparison of five different methods for delivering medical aid to persons in need during a large scale emergency scenario. The first four methods, namely Gurobi, Greedy, 3SH, and MCGRH, are prior art. The fifth method in table 5, namely MCGH, is the method of the present disclosure.

The MCGH was implemented using Python programming language. The results of table 5 were produced by utilizing a computer with an Intel Core i7 processor running at 3.1 GHz using 16 GB 2133 MHz LPDDR3 of RAM running Macintosh HD. SPSS version 28.0.0.0 was used for statistical analysis where the non-parametric Wilcoxon signed-rank test is performed at a 5% level of significance.

The parameters used for the drones in the example of table 5 are based on table 6 below.

TABLE 6

| The drone parameters assumed. | |
|---|---|
| Power transfer efficiency ($\eta$) | 0.66 |
| Lift-to-drag ratio ($\theta_s$) | 3.5 |
| Tare weight | 10.1 kg |
| Maximum payload | 5 kg |
| Battery capacity | 777 W h | c is the capacity that each facility can offer, which is calculated based on the total demand weight of patients $w_i$ and the number of facilities to be opened p, as shown in Equation (15).

The traveling distance between a patient and a potential facility was calculated in miles by using the Euclidean distance based on the latitude and longitude of their locations. It was assumed that there were no obstacles on the way.

The twenty-two runs (or instances, or performances of the methods indicated in table 5) are grouped by the number of opened facilities p followed by the number of available drones K. Table shows the performance of the four methods as measured by time (in seconds) and coverage. The Gurobi MIP is an exact solution method that runs until a solution is found or a limit of 7,200 seconds is reached. 3SH and

TABLE 5

Comparison of Gurobi, Greedy heuristic, 3SH, MCGRH and MCGH in terms of time(s) and percentage of coverage; best values are shown in bold font for each instance, p is the number of the opened facilities, and K is number of the available drones.

| p | \|K\| | Gurobi Time (s) | Gurobi Coverage (%) | Greedy Time (s) | Greedy Coverage (%) | 3SH Time (s) Avg | 3SH Coverage (%) Avg | MCGRH Time (s) Avg | MCGRH Coverage (%) Avg | MCGH Time (s) | MCGH Coverage (%) |
|---|---|---|---|---|---|---|---|---|---|---|---|
| 5 | 20 | 7200 | 56.4 | 0.1 | 45.2 | 14.7 | 54.5 | 0.67 | 51.53 | 0.66 | 55.50 |
| 5 | 25 | 7200 | 61.9 | 0.1 | 50.3 | 15.9 | 59.5 | 0.61 | 57.89 | 0.71 | 61.70 |
| 5 | 30 | 7200 | 66.3 | 0.1 | 55.3 | 16.7 | 63.7 | 0.67 | 63.38 | 0.70 | 67.50 |
| 5 | 35 | 7200 | 70.2 | 0.1 | 58.9 | 18.3 | 67 | 0.69 | 68.09 | 0.63 | 71.60 |
| 5 | 40 | 7200 | 72.7 | 0.1 | 62.5 | 18.8 | 69.9 | 0.67 | 71.02 | 0.66 | 75.60 |
| 10 | 20 | 7200 | 64.4 | 0.2 | 48.2 | 16.6 | 61.4 | 0.70 | 57.36 | 0.75 | 59.60 |
| 10 | 30 | 7200 | 75 | 0.2 | 59.8 | 18.3 | 71.5 | 0.80 | 69.98 | 0.74 | 71.40 |
| 10 | 40 | 7200 | 83.8 | 0.2 | 67.1 | 20.1 | 78.4 | 0.85 | 79.15 | 0.77 | 81.90 |
| 15 | 30 | 7200 | 79.7 | 0.2 | 59.2 | 21.9 | 75.2 | 1.05 | 72.40 | 0.88 | 75.70 |
| 15 | 45 | 7200 | 90.2 | 0.2 | 73.1 | 24.3 | 83.9 | 0.92 | 86.43 | 0.87 | 89.50 |
| 15 | 60 | 7200 | 92.6 | 0.3 | 73.1 | 24.8 | 85 | 1.07 | 90.43 | 0.91 | 94.70 |
| 20 | 20 | 7200 | 71.2 | 0.3 | 52.8 | 25.1 | 65.8 | 1.04 | 59.32 | 0.99 | 63.00 |
| 20 | 40 | 7200 | 90.4 | 0.3 | 70.7 | 28.7 | 84.2 | 1.03 | 83.77 | 0.99 | 85.10 |
| 20 | 60 | 320 | 93.8 | 0.3 | 72.2 | 30.4 | 87.2 | 1.06 | 92.33 | 1.02 | 94.50 |
| 20 | 80 | 36 | 93.8 | 0.4 | 72.2 | 30.9 | 87.5 | 1.03 | 91.36 | 1.03 | 94.50 |
| 25 | 25 | 7200 | 79.6 | 0.3 | 53.6 | 33 | 71.5 | 1.10 | 67.70 | 1.13 | 66.60 |
| 25 | 50 | 337 | 93.8 | 0.4 | 71.4 | 36.6 | 88.9 | 1.21 | 90.94 | 1.13 | 90.00 |
| 25 | 75 | 27 | 93.8 | 0.5 | 71.4 | 37.4 | 88.2 | 1.23 | 92.21 | 1.08 | 92.30 |
| 25 | 100 | 43 | 93.8 | 0.5 | 71.4 | 38.1 | 89.5 | 1.24 | 92.16 | 1.13 | 92.30 |
| 30 | 30 | 7200 | 85.3 | 0.3 | 60.6 | 40.3 | 76.8 | 1.31 | 72.24 | 1.23 | 66.90 |
| 30 | 60 | 23 | 93.8 | 0.5 | 74.8 | 44.3 | 90.9 | 1.47 | 93.21 | 1.30 | 92.20 |
| 30 | 90 | 31 | 93.8 | 0.6 | 74.7 | 45. | 90.7 | 1.22 | 92.87 | 1.50 | 92.50 |
| Average | | 4946.23 | 81.65 | 0.28 | 63.57 | 27.29 | 76.87 | 0.98 | 77.08 | 0.95 | 78.85 |

MCGRH are not deterministic, so the table shows their average results over 30 different runs of each instance. The Greedy and the MCGH are deterministic solution methods, so each was executed once until termination conditions are satisfied. The best result of each instance is highlighted in bold font in table 5.

In table 5, coverage is the percentage of the total accommodated patients demand. The Greedy algorithm in table 5 has the best time performance, albeit with very weak coverage compared to the other methods. Gurobi in table 5 is the best of the three methods in terms of coverage but was associated with the worst time performance. 3SH achieved a coverage of 94.15% of Gurobi's solutions on average, whereas when compared with Gurobi's time performance, 3SH took only approximately 27 seconds on average. On the other hand, the MCGRH achieved a coverage of 94.4% of Gurobi's solutions on average.

Notably, in table 5, the MCGH (the method of the present disclosure) achieved a higher percentage of coverage than Gurobi in six instances with lower time performance. Clearly, in these instances, MCGH exhibited superior time performance compared to Gurobi, making the performances incomparable. Where Gurobi required varying times for these cases (i.e., to run the algorithm), including 7200 s, 7200 s, 7200 s, 7200 s, 320 s, and 36 s, MCGH completed them in 0.70 s, 0.63 s, 0.66 s, 0.91 s, 1.02 s, and 1.03 s, respectively. That is, it took only 0.70 s, 0.63 s, 0.66 s, 0.91 s, 1.02 s, and 1.03 s, respectively, for the computer to run the MCGH algorithms 1-3 of the present disclosure to find a reasonable solution. The difference between about 1 second or less for the method of the present disclosure and to 7200 seconds (to 36 seconds) for Gurobi is a stark difference. The method of the present disclosure can be performed exceedingly quickly due to the method steps described in this specification and provide excellent coverage results.

In addition, the MCGH runs, as tabulated in table 5, achieved a coverage of 96.6% of Gurobi's solutions on average. As illustrated in table 5, the MCGH additionally exceeded the coverage of the MCGRH in 17 out of 22 instances with better average coverage.

Based on the results laid out in table 5, it is clear that the MCGH stands out due to its notably low calculation time paired with high coverage, where it was able to achieve a coverage of 94.7%, whereas the optimal coverage was 95.7% (as explained before) was achieved in less than one second of calculation time. The other methods, as illustrated in FIG. 5, did not reach this percentage of coverage.

Therefore, the method of the present specification is highly effective as reducing the computational run time while providing a high degree of coverage of patients in an emergency medical scenario.

In an approach, step S115 includes using a computer system, for example, the computer system of the administrator 100, for loading the at least one assigned drone with medication for each covered patient of each marked facility, and for launching the loaded at least one assigned drone to each said covered patient of each marked facility. In this approach, the loading with medication of each assigned drone for each covered patient can be carried out by using the computer system, and/or the launching of each loaded drone can be carried out by using the computer system.

In the approach where the computer system is used for loading and/or launching the drones, at each facility marked to be used as a drone launching center, a conveyor belt 602 (see FIG. 6) can be used to move one or more medication containers 610 (or 610_1 to 610_N, where N is a positive nonzero integer, when the conveyor belt 602 will be used to load medication in containers for more than one covered patient) along a conveying direction C. Each one of the medication containers 610_1-610_N can be filled with the medication for one covered patient, from among the plurality of covered patients, at a medication filling station (or chute) 620.

The medication filling station 620 may be disposed on (e.g., above) or adjacent to the conveyor belt 602 to discharge the medication for each covered patient into one of the medication containers 610_1-610_N (e.g., to discharge medication for each covered patient in a predetermined container from among the medication containers 610_1-610_N) when a particular medication container 610 is arranged in a position to be loaded by the medication filling station 620 (e.g., when a medication container 610 is positioned under the medication filling station 620) due to the movement of the conveyor belt 602.

Figure 6:
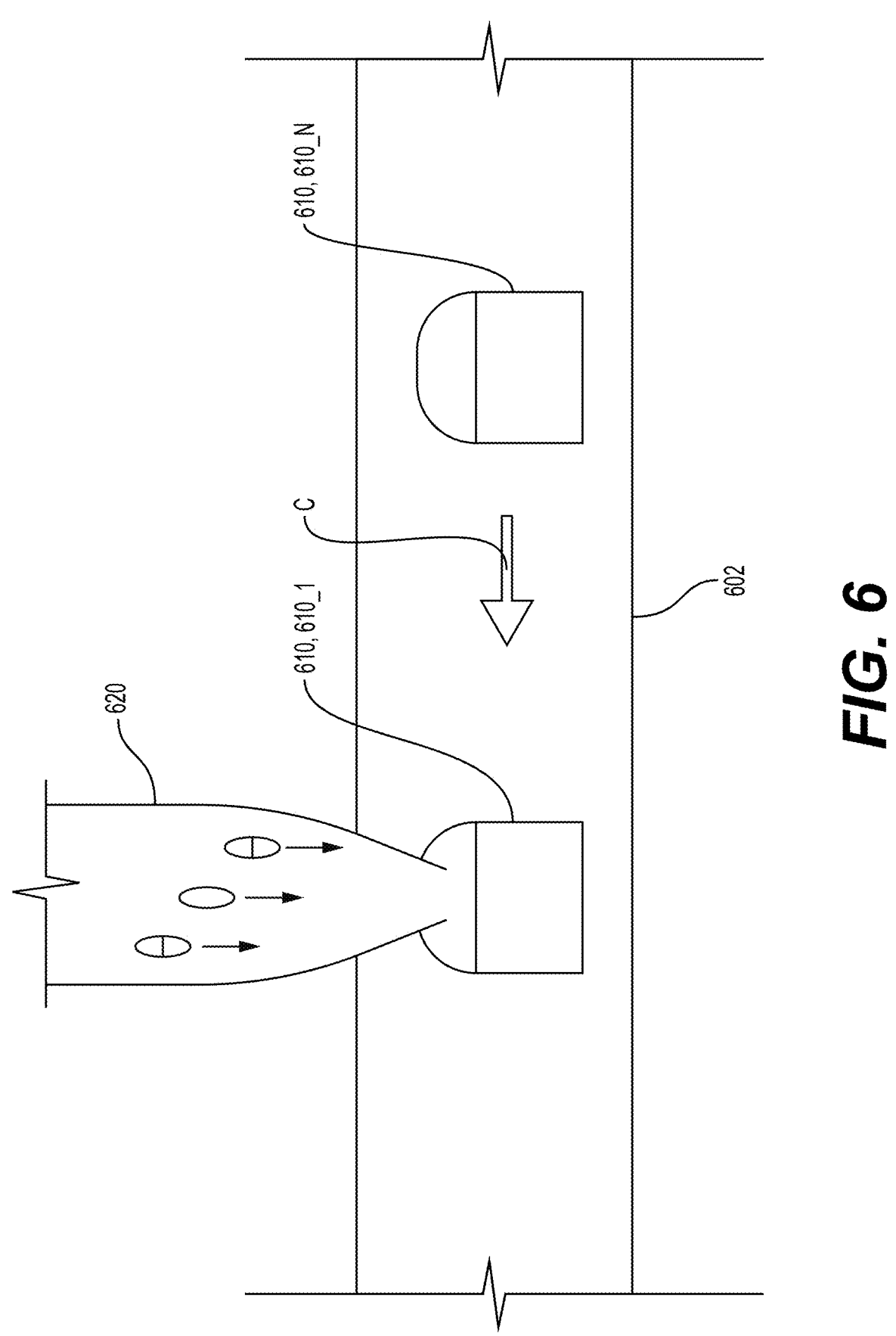
FIG. 6 is a diagram illustrating medication containers being filled with medication for delivery to patients in accordance with an exemplary embodiment of the present disclosure.

As a non-limiting example, and with reference to FIG. 6, at facility_3 illustrated in FIG. 5, the computer system of the administrator 100 may be configured to: a) move a medication container 610_6 on the conveyor belt 602 until the container 610_6 is positioned under the medication filling station 620, b) stop the container 610_6 under the medication filling station 620, c) release the medication needed for patient_6 (who is associated with facility_3 and with the medication container 610_6) into the medication container 610_6, and d) resume the movement of the conveyor belt 602 in the direction C. The location of each container 610 on the conveyor belt 602 can be monitored such that the position of each container 610 on the conveyor belt 602 is known. This loading process can be repeated for each medication container that will be used to carry medication for each covered patient at each facility that can be used as a drone launching center.

Figure 7:
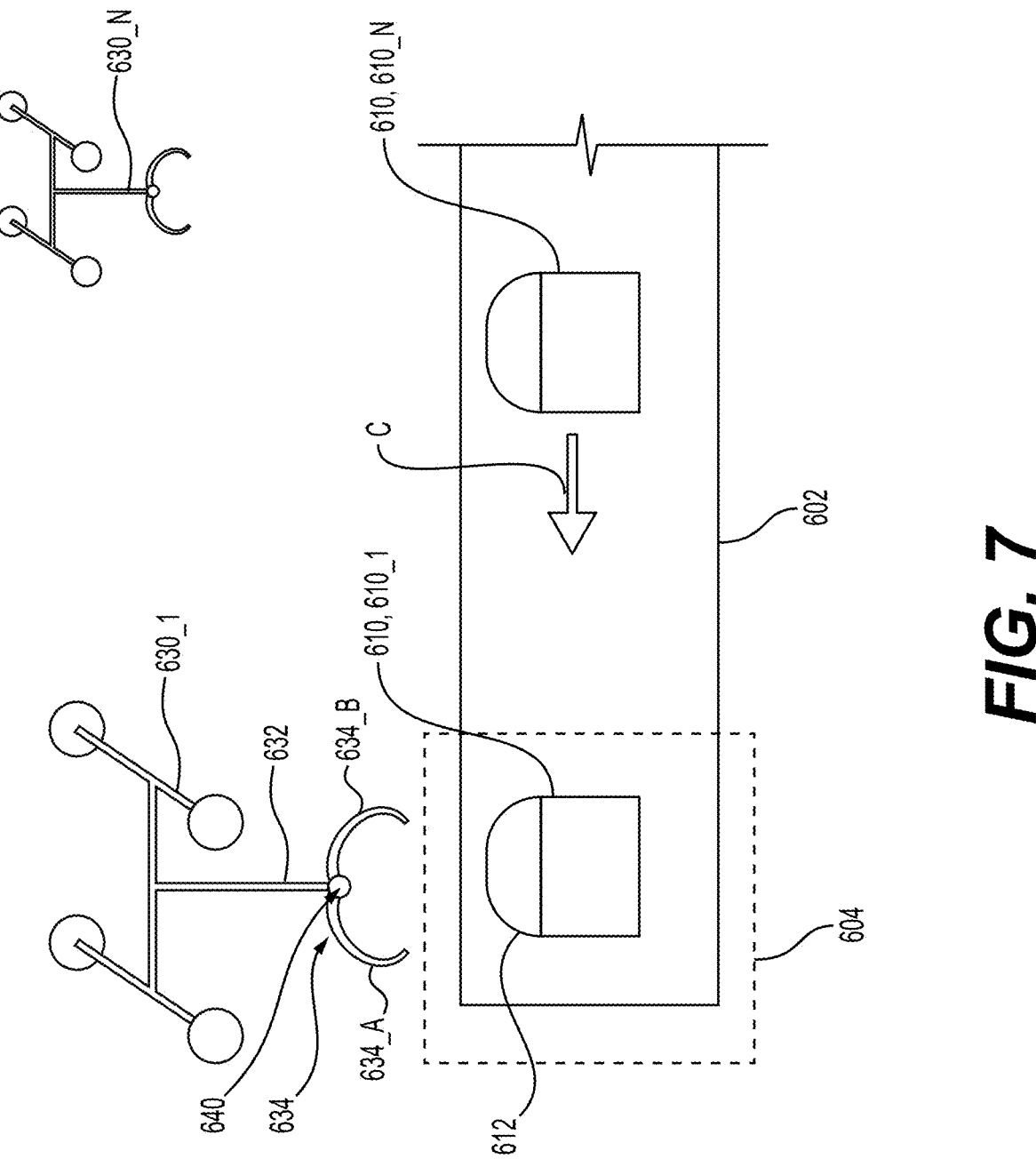
FIG. 7 is diagram illustrating drones in a process of being loaded with medication containers in accordance with an exemplary embodiment of the present disclosure.

Referring to FIG. 7, once that the containers 610_1-610_N at each facility that can be used as a drone launching center are filled with medication for the covered patients, the conveyor belt 602 may be used to convey each container 610_1-610_N to a drone launching pad 604.

The three-dimensional coordinates of the drone launching pad 604 may be known. For example, the latitude and longitude coordinates of the drone launching pad may be known together with the altitude of the drone launching pad 604.

Referring to FIG. 7, the computer system may be configured to move or direct (e.g., fly) each assigned drone (e.g., assigned drones 630_1 to 630_N, with N being a nonzero positive integer) to the drone launching pad 604 of each facility marked to be used as a drone launching center.

Figure 8:
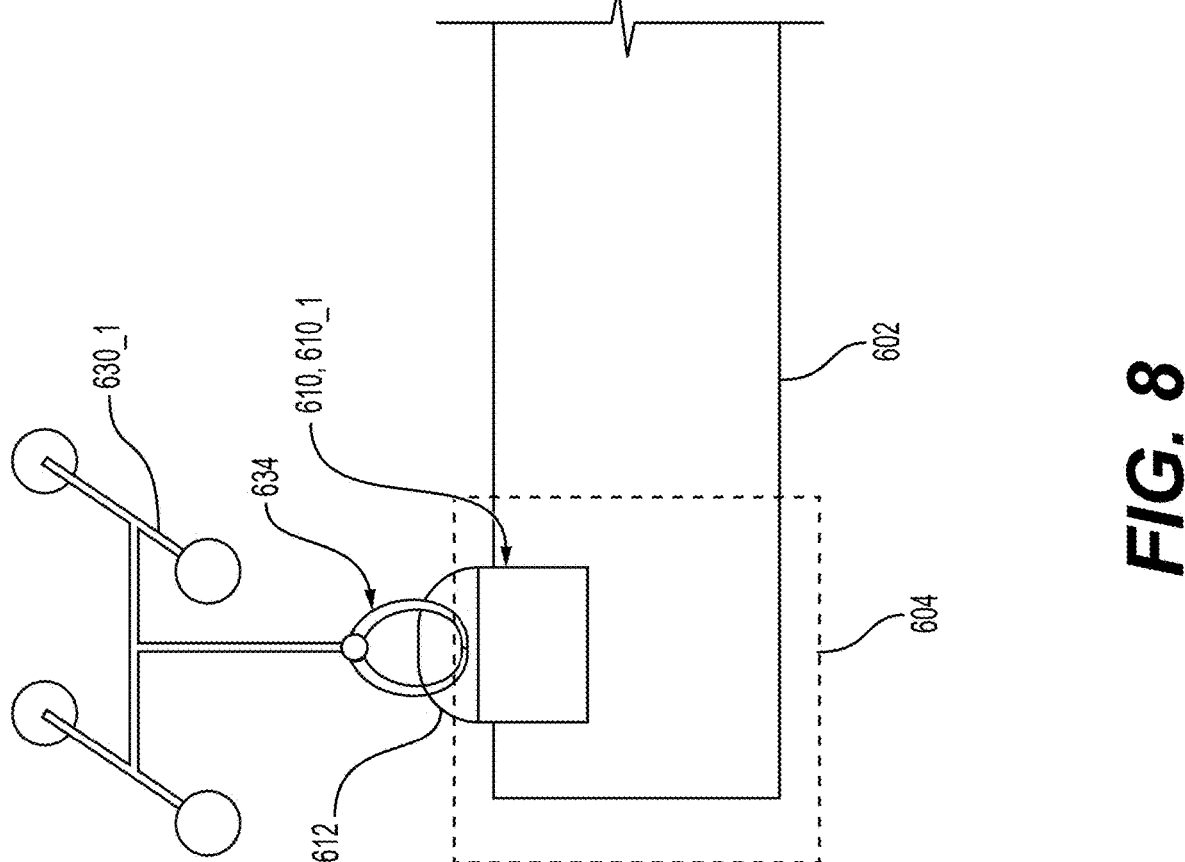
FIG. 8 is a diagram illustrating a drone in a connected state with a medication container in accordance with an exemplary embodiment of the present disclosure.

Referring to FIG. 7, each drone from among the drones 630_1 to 630_N may have a cord 632 and a selectively operable locking structure 634. The selectively locking structure 634 may have a first structural member 634_A and a second structural member 634_B. The first and second structural members 634A, 634B can be selectively moved between an open state, as illustrated in FIG. 7, and a closed state, as illustrated in FIG. 8, by an electrical motor 640.

Each drone, from among the drones 630_1 to 630_N, may include a cord 632. The cord 632 is configured to transmit electrical power to the motor 640 to operate the motor 640 to open and close the locking structure 634. The cord 632 is also configured to provide structural strength to support the weight of a medication container 610.

Once that a particular medication container 610 is transferred to the drone launching pad 604 of a particular facility that will be used as a drone launching center, the computer system may be configured to direct a drone associated with the package (or medication container 610) located at the launching pa d 604 toward the launching pad 604 to pick up (or load) the medication container 610.

For example, drone 630_1 can be used to pick up (or load) medication container 610_1, drone 630_2 can be used to pick up medication container 610_2, and so on, at each facility that will be used as a drone launching center.

Since the coordinates (e.g., GPS coordinates) of the drone launching pa d 604 are known at each facility that will be used as a drone launching center, and the drones 630_1-630_N may include a position tracking sensor such as a GPS, sensor, a GLONASS sensor, or the like, a drone 630 associated with the medication container 610 of a covered patient (it is known when a particular medication container 610 is located on the drone launching pad 604) can be instructed by the computer system to fly to the launching pad 604 to pick up (or load) the medication container 610.

For example, the drone 630_1 can approach the drone launching pad 604 with the selectively operable locking structure 634 in the open state, as illustrated in FIG. 7. The dimensions of the medication container 610_1 (and the dimensions of every other medication container 610) are known, including a height of the handle 612 of each medication container 610. As such, the computer system can be used to instruct the drone 630_1 to position the selectively operable locking structure 634 over the handle 612 of the container 610_1 and then to close the selectively operable locking structure 634. The closing of the electively operable locking structure 634 will cause the drone 630_1 to be structurally connected to the medication container 610_1. See FIG. 8, illustrating the drone 630_1 connected to the medication container 610_1

A load cell included in each drone 630 and connected to the cord 632 can be used to confirm a successful engagement between each drone 630 and each container 610. The process of using the computer system to load (or connect) the medication container 610_1 to the drone 630_1 as described in this specification can be repeated by using the computer system to load each drone from among the drones 630_1 to 630_N to each its corresponding medication container 610, from among the medication containers 610_1 to 610_N. The loading process can be performed, for example, sequentially for each of the drones 630.

Figure 9:
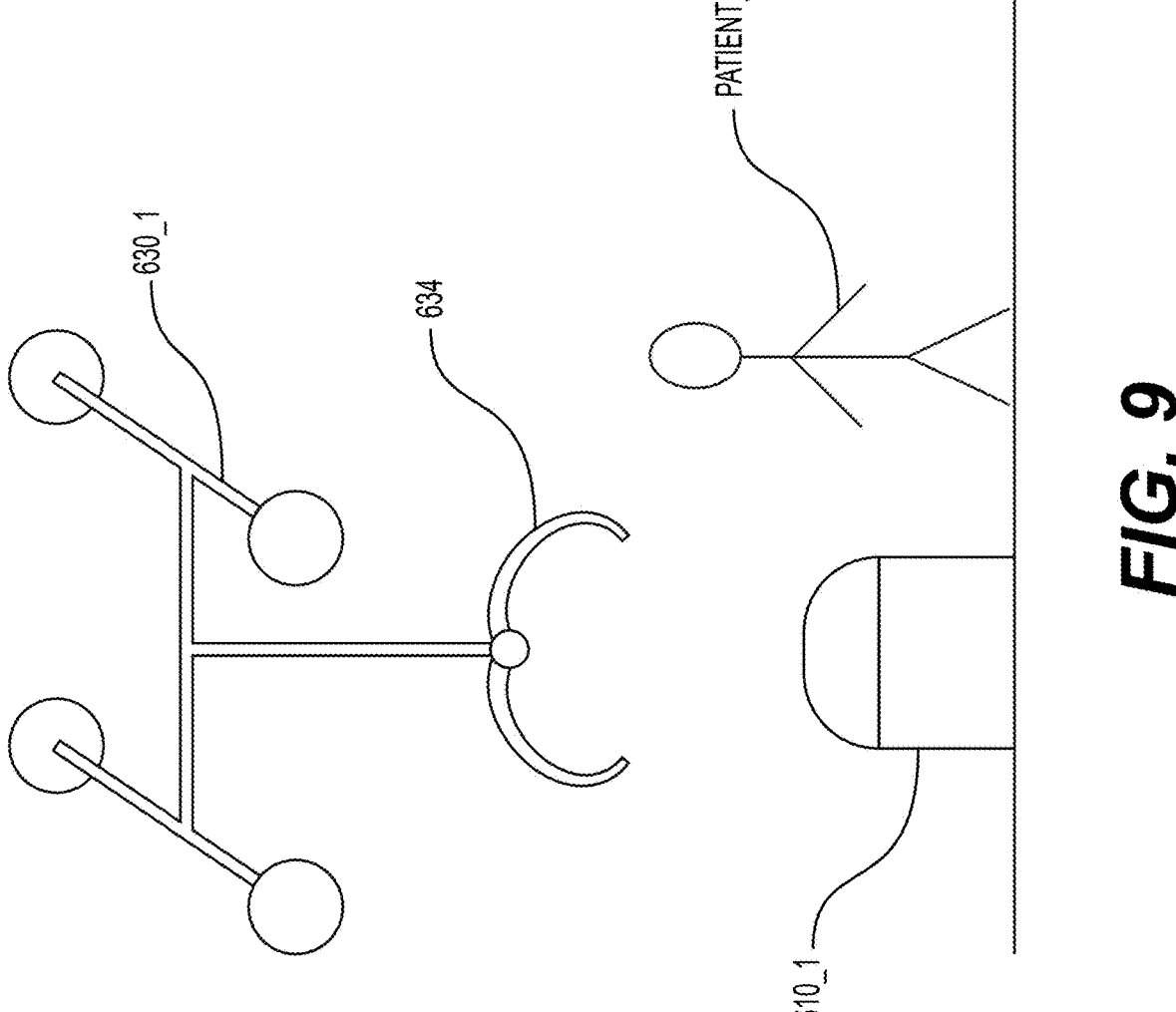
FIG. 9 is a diagram illustrating a drone having delivered a medication container in accordance with an exemplary embodiment of the present disclosure.

Subsequent to the loading of each drone 630_1-630_N with its respective medication container 610, the computer system can be used to fly each drone toward each covered patient to bring the medication contained in the container 610 to each patient. When arriving at the location of each patient, each drone 630 can release the medication container 610 by selectively opening the locking structure 634, as controlled by using the computer system For example, FIG. 9 exemplarily illustrates drone 630_1 having released the medication container 610_1 for patient_1 when arriving at the location of patient_1 by selectively opening the locking structure 634 adjacent to the location of patient_1.

Subsequent to dropping off a medication container 610 to a patient, each drone 630 can be flown back to a facility used as a drone launching center for picking up an additional medication container 610 for delivery to an additional patient, or for recharging, depending on the battery level of the drone, as determined by using the method taught by this specification and as operated by using the computer system taught by this specification.

While the present disclosure has been particularly shown and described with reference to exemplary embodiments thereof, it will be apparent to those of ordinary skill in the art that various changes in form and detail may be made therein without departing from the spirit and scope of the present disclosure as defined by the following claims.

What is claimed is:

1. A computer-implemented method for delivering medication or medical supplies to persons in need thereof by using drones, the computer performing each of the method steps comprising:

receiving patient data, the patient data including a plurality of patients in need of medical assistance, and for each one of the plurality of patients, the patient data includes a location of the patient and a description of a type of medical assistance needed;

receiving drone data, the drone data including a plurality of drones that can be used to deliver medication to the plurality of patients;

receiving facility data, the facility data including one or more facilities located in an area capable of providing the medication to the plurality of patients, wherein the facility data further includes an indication of which facility, from among the one or more facilities included in the facility data, can be used as a drone launching center;

selecting one or more facilities to be used to provide the medication to the plurality of patients, from among the facilities that can be used as a drone launching center, based on the received patient data and the received facility data, wherein the selected one or more facilities will be used as drone launching centers to deliver the medication to the plurality of patients via the plurality of drones;

assigning at least one patient, from among the plurality of patients, to each facility from among the selected one or more facilities;

assigning at least one drone, from the plurality of drones, to each facility from among the selected one or more facilities;

assigning at least one patient to each drone, from among the at least one patient and the at least one drone assigned to each facility at each one of the selected one or more facilities, wherein the selecting of the one or more facilities to be used includes:

calculating a total weight demand of the medication that each facility can provide for potential patients, from among the plurality of patients, for each facility that can be used as a drone launching center, selecting a facility that can supply a highest total weigh demand of the medication from the facilities that can be used as a drone launching center, marking the selected facility as a facility that will be used as a drone launching center, and marking one or more patients whose weight demand of the medication can be met by the marked drone launching center as covered patients, and when additional patients that are not marked as being covered remain, from among the plurality of patients, seek to cover an uncovered patient with a highest weight demand of the medication, from among the patients not marked as being covered, by the marked drone launching center if the marked drone launching center has capacity to supply the weight demand of medication for the uncovered patient, and mark the uncovered patient as being covered when the marked drone launching center has capacity to supply the weight demand of medication for the uncovered patient, or when the marked drone launching center does not have the capacity to supply the weight demand of medication for the uncovered patient, select an additional facility that can supply a highest total weigh demand of medication, from among the facilities that can be used as drone launching centers but are not yet marked as facilities that will be used as drone launching centers, mark the selected additional facility as a facility that will be used as a drone launching center, and mark the uncovered patient as being covered by said marked additional facility;

flying the at least one assigned drone to a launching pad based on a position tracking sensor of the at least one assigned drone and position coordinates of the launching pad;

loading the at least one assigned drone with the medication for each covered patient of each marked facility by positioning a locking structure in an open state of the at least one assigned drone over a handle of a container with the medication at the launching pad, and closing the locking structure of the at least one assigned drone; and flying the loaded at least one assigned drone to each said covered patient of each marked facility, and opening the locking structure of the at least one assigned drone to release the container with the medication.

2. The method of claim 1, wherein the calculating of the total weight demand of medication for each facility that can be used as a drone launching center is performed once.

3. A computer-implemented method for delivering medication or medical supplies to persons in need thereof by using drones, the computer performing each of the method steps comprising:

receiving patient data, the patient data including a plurality of patients in need of medical assistance, and for each one of the plurality of patients, the patient data includes a location of the patient and a description of a type of medical assistance needed;

receiving drone data, the drone data including a plurality of drones that can be used to deliver medication to the plurality of patients based on the description of the type of medical assistance needed;

receiving facility data, the facility data including one or more facilities located in an area capable of providing the medication to the plurality of patients, wherein the facility data further includes an indication of which facility, from among the one or more facilities included in the facility data, can be used as a drone launching center;

selecting one or more facilities to be used to provide the medication to the plurality of patients, from among the facilities that can be used as a drone launching center, based on the received patient data and the received facility data, wherein the selected one or more facilities will be used as drone launching centers to provide the medication to the plurality of patients via the plurality of drones;

assigning at least one patient, from among the plurality of patients, to each facility from among the selected one or more facilities;

assigning at least one drone, from the plurality of drones, to each facility from among the selected one or more facilities;

assigning at least one patient to each drone, from among the at least one patient and the at least one drone assigned to each facility at each one of the selected one or more facilities, wherein the selecting of the one or more facilities includes:

calculating a total weight demand of the medication that each facility can provide for potential patients, from among the plurality of patients, for each facility that can be used as a drone launching center, selecting a first facility that can supply a highest total weigh demand of the medication from the facilities that can be used as a drone launching center, marking the selected first facility as a facility that will be used as a drone launching center, and marking one or more patients whose weight demand of the medication can be met by the first facility as covered patients, and when additional patients that are not marked as being covered remain, from the plurality of patients, seek to cover an uncovered patient with a highest weight demand of the medication, from among the patients not marked as being covered, by the first facility if the first facility has capacity to supply the weight demand of medication for the uncovered patient, and mark the uncovered patient as being covered when the first facility has capacity to supply the weight demand of medication for the uncovered patient, or when the first facility does not have the capacity to supply the weight demand of medication for the uncovered patient, select a second facility that can supply a highest total weigh demand of medication, from among the facilities that can be used as drone launching centers but are not yet marked as facilities that will be used as drone launching centers, mark the second facility as a facility that will be used as a drone launching center, and mark the uncovered patient as being covered by the second facility;

flying the at least one assigned drone to a launching pad based on a position tracking sensor of the at least one assigned drone and position coordinates of the launching pad;

loading the at least one assigned drone with the medication for each covered patient of each marked facility by positioning a locking structure in an open state of the at least one assigned drone over a handle of a container with the medication at the launching pad, and closing the locking structure of the at least one assigned drone; and flying the loaded at least one assigned drone to each said covered patient of each marked facility, and opening the locking structure of the at least one assigned drone to release the container with the medication.

4. The method of claim 3, wherein the calculating of the total weight demand of medication for each facility that can be used as a drone launching center is performed once.

5. A system for delivering medication or medical supplies to persons in need thereof, the system comprising:

medication;

a plurality of drones that can be used to deliver the medication to a plurality of patients in need of medical assistance; and a computer system comprising a processor and a non-transitory, tangible, program storage medium, readable by the computer system, embodying a program of instructions executable by the processor of the computer system to perform method steps for delivering the medication or medical supplies to persons in need thereof, the method comprising:

receiving patient data, the patient data listing the plurality of patients in need of medical assistance, and for each one of the listed patients, the patient data includes a location of the patient and a description of a type of medical assistance needed;

receiving drone data, the drone data listing the plurality of drones that can be used to deliver medication to the plurality of patients based on the description of the type of medical assistance needed;

receiving facility data, the facility data listing one or more facilities located in an area capable of providing the medication to the plurality of patients, wherein the facility data further includes an indication of which facility, from among the one or more facilities included in the facility data, can be used as a drone launching center;

selecting one or more facilities to be used to provide the medication to the plurality of patients, from among the facilities that can be used as a drone launching center, based on the received patient data and the received facility data, wherein the selected one or more facilities will be used as drone launching centers to provide the medication to the plurality of patients via the plurality of drones;

assigning at least one patient, from among the plurality of patients, to each facility from among the selected one or more facilities;

assigning at least one drone, from the plurality of drones, to each facility from among the selected one or more facilities;

assigning at least one patient to each drone, from among the at least one patient and the at least one drone assigned to each facility at each one of the selected one or more facilities;

wherein the selecting of the one or more facilities includes:

calculating a total weight demand of the medication that each facility can provide for potential patients, from among the plurality of patients, for each facility that can be used as a drone launching center, selecting a first facility that can supply a highest total weigh demand of the medication from the facilities that can be used as a drone launching center, marking the selected first facility as a facility that will be used as a drone launching center, and marking one or more patients whose weight demand of the medication can be met by the first facility as covered patients, and when additional patients that are not marked as being covered remain, from the plurality of patients, seek to cover an uncovered patient with a highest weight demand of the medication, from among the patients not marked as being covered, by the first facility if the first facility has capacity to supply the weight demand of medication for the uncovered patient, and mark the uncovered patient as being covered when the first facility has capacity to supply the weight demand of medication for the uncovered patient, or when the first facility does not have the capacity to supply the weight demand of medication for the uncovered patient, select a second facility that can supply a highest total weigh demand of medication, from among the facilities that can be used as drone launching centers but are not yet marked as facilities that will be used as drone launching centers, mark the second facility as a facility that will be used as a drone launching center, and mark the uncovered patient as being covered by the second facility;

flying the at least one assigned drone to a launching pad based on a position tracking sensor of the at least one assigned drone and position coordinates of the launching pad;

loading the at least one assigned drone with the medication for each covered patient of each marked facility by positioning a locking structure in an open state of the at least one assigned drone over a handle of a container with the medication at the launching pad, and closing the locking structure of the at least one assigned drone; and flying the loaded at least one assigned drone to each said covered patient of each marked facility, and opening the locking structure of the at least one assigned drone to release the container with the medication.

6. The system of claim 5, wherein the calculating of the total weight demand of medication for each facility that can be used as a drone launching center is performed once.

* * * * *